United States Patent [19]

Miller

[11] 3,939,832

[45] Feb. 24, 1976

[54] LIQUID FLOW REGULATOR AND MONITOR FOR INFUSION SYSTEM

[75] Inventor: John J. Miller, Marietta, Ohio

[73] Assignee: Med-Pak Corporation, Charleston, W. Va.

[22] Filed: Mar. 9, 1973

[21] Appl. No.: 339,839

[52] U.S. Cl. ............................................. 128/214 R
[51] Int. Cl.² ......................................... A61M 5/00
[58] Field of Search ........ 128/214 R, 214 C, 214 E, 128/214.2, 221, 133; 251/4–10

[56] References Cited
UNITED STATES PATENTS

| | | | |
|---|---|---|---|
| 2,261,213 | 11/1941 | Bierman | 128/214 R |
| 2,449,882 | 9/1948 | Daniels | 128/133 |
| 2,771,878 | 11/1956 | Folland et al. | 128/214 R |
| 3,048,171 | 8/1962 | Grau | 128/214.2 |
| 3,299,904 | 1/1967 | Burke | 251/9 X |
| 3,348,543 | 10/1967 | Stafford | 128/214 R |
| 3,507,278 | 4/1970 | Werding | 128/214 F |
| 3,543,753 | 12/1970 | Weinstein | 128/214 F |

Primary Examiner—Dalton L. Truluck
Attorney, Agent, or Firm—Cennamo Kremblas & Foster

[57] ABSTRACT

Apparatus for use in hospitals and the like for administering to a patient medicated liquid. The improvement comprises a control for regulating and visually indicating the rate of fluid flow into the body. The system is equally applicable to intravenous, intrarterial, or subcutaneous. A positive action liquid control valve together with a flow meter is positioned on the patient adjacent the point of entry of the fluid into the body. The apparatus — adaptable to the commercial single use disposeable kits — in its preferred embodiment, is strapped to the wrist of the patient. The apparatus is further adapted to receive the conventional injection needle for the addition of other medication.

7 Claims, 4 Drawing Figures

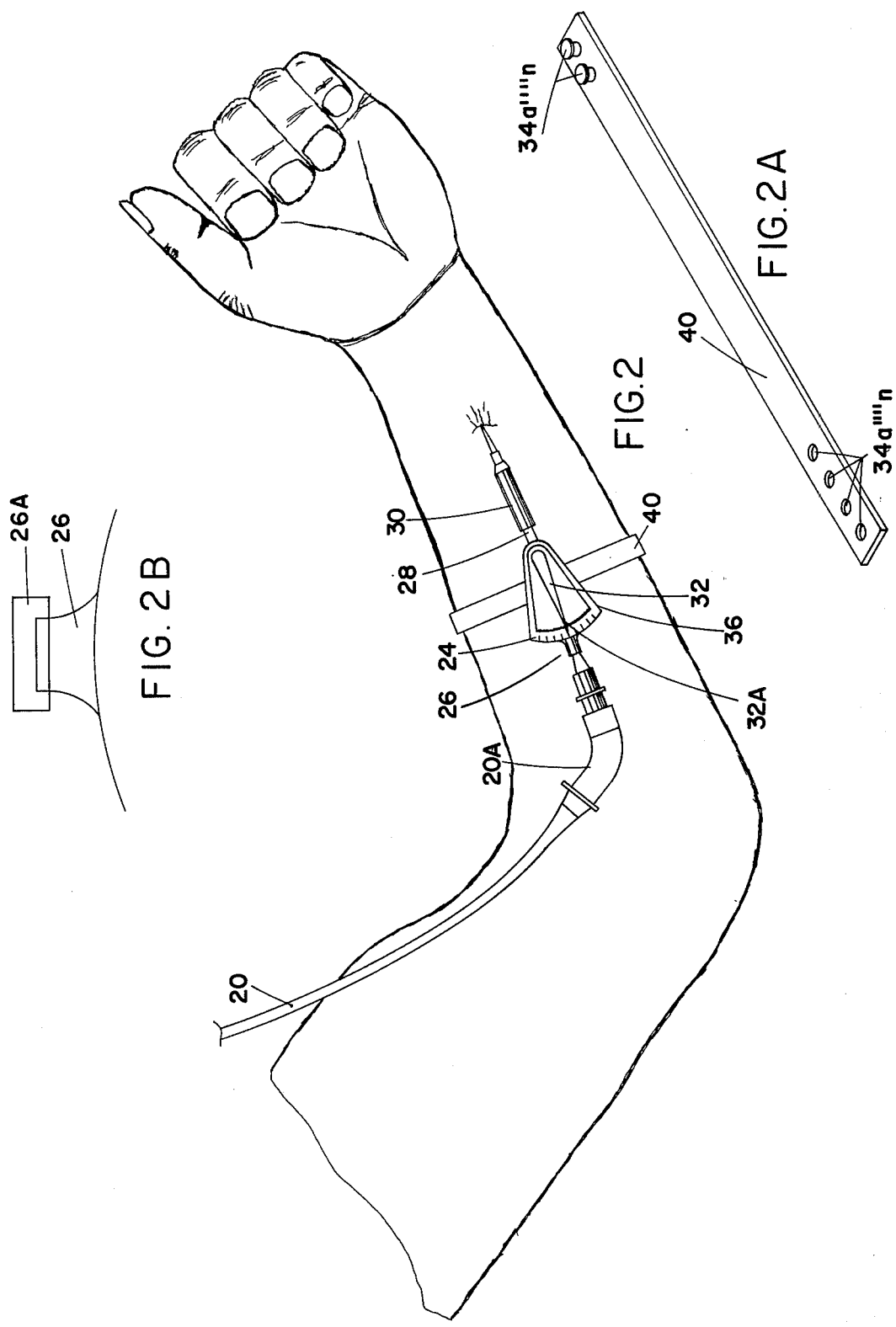

LIQUID FLOW REGULATOR AND MONITOR FOR INFUSION SYSTEM

BACKGROUND

Liquids are administered in hospitals to patients for many purposes — the most common perhaps being the intravenous fluid infusion. These infusion systems generally include an inverted glass bottle filled with sterile liquid such as salt, mineral, sugar solution, electrolytes, and antibiotics. As the solution is drained from an intravenous bottle through the flexible tube for infusion into the patient through a needle in the patient's vein, air is vented into the bottle for displacement of the fluid drained from the bottle. Other bottles in use are of the collapsible type and hence do not require the replacement of air. Commercial apparatus on the market also include disposeable kits that comprise a plastic tubing with a means at one end for entering the bottle to drain the fluid and an air inlet to replace the fluid as it is drained. At the other end of the tube means are provided to connect with an injection needle.

PRIOR ART

The most common technique for metering the liquid output from conventional intravenous bottles has the human process. This comprises the operator mentally counting the number of drops falling into the drip chamber of the intravenous bottle during a predetermined time period. The manually manipulated mechanical valve in the liquid output tube controls or stops the flow of liquid through the tubing. The drip rate from an intravenous bottle often tends to vary over a period of time due to changes in the bottle height and changes in resistance to flow in the system or patient. The suggested systems and apparatus for the elimination of the manual counting of the drop rate of an intravenous bottle are complex in nature. Each system known requires the regulating and monitoring the liquid flow through the liquid output tube leading to the patient. Such devices have ranged from those which physically sense the passage of liquid drops through the drip chamber of the intravenous bottle to flowmeter devices which are physically inserted in the tube leading from the liquid output of the intravenous bottle to the patient.

Prior devices installed in the liquid output tube are required to be sterile, and have often required expensive filters which tend to clog when heavy liquids are passed. Also flow-metering systems installed in the liquid output of corporeal infusion systems have tended to be difficult to both calibrate and operate due to variances in liquid viscosity from one type of infusion to another.

Although more elaborate and perhaps sophisticated systems of measuring the liquid flow have been proposed, the improvements — as noted — are generally at the sacrifice of something else. Also since the drip chamber and the shut off valve are generally adjacent the liquid container, a substantial amount of unmeasured liquid in the line (from the stopper to the needle) may be administered to the patient. Alternatively, if this excess liquid is drained there is a possibility that air may be injected into the veins of the patient.

The above-mentioned mechanical valve is extremely erratic due to slippage — and most importantly, crimp the line. Other medical, technical, or mechanical reasons cause variations in liquid flow from the container to the patient and erratic replacement of air to the container. In addition, any break of the seal or the liquid supply system between the control valve and the body entry point may permit air to enter and mix with the liquid and flow into the body. This can easily happen when strain is applied to the connections of present infusion systems or by cuts in the tubing by sharp surgical instruments common to operating rooms. Accordingly, proper administration requires frequent or continuous attendance of a nurse and in some instances a physician.

Also in present day medical practice, it is customary to utilize an intravenous opening in the tubing for the injection of medication — in lieu of the hyperdermic needle. The primary benefit being the time control of the medication into the body and the elimination of further injections.

SUMMARY OF INVENTION

The present invention, in its preferred embodiment, is particularly adaptable to the present day commercial apparatus for the administration or infusion of fluids into the body. The improvements alleviate the above-noted disadvantages of the regulating and metering devices in use. Particularly a flow meter and a control valve are inserted at or immediately adjacent to the entry point to the patients body. This may be either at the needle — or as in certain instances — to a catheter. The flow meter and the control valve are in themselves incorporated in an arm band to be worn by the patient.

The flow meter, at the body end of the tubing indicates the exact amount of liquid entering the body — irrespectfully of whether or not the flow through the tubing has been impeded. The control valve is a positive on/off and partial valve positioned at the end of the tubing and hence does not pinch or crimp in any way impede the liquid flow through the tubing.

OBJECTS

It is accordingly a principal object of the present invention to provide a new and improved reliable apparatus for controlling the infusion of liquids into the body of the patient.

A further object of the invention is to provide such apparatus that is compatable with and does not change in any way commercial apparatus for infusion of liquids presently marketed.

Another object of the invention is to measurably control the fluids infused into the body without the attended disadvantages noted in the prior art.

Other objects and features of the present invention will become apparent from the following detailed description when taken in conjunction with the drawings in which:

BRIEF DESCRIPTION OF DRAWINGS

FIGS. 2, 2A and 2B are enlarged illustrations of the preferred embodiment of the invention.

DESCRIPTION OF THE PREFERRED EMBODIMENTS

Figure 1:
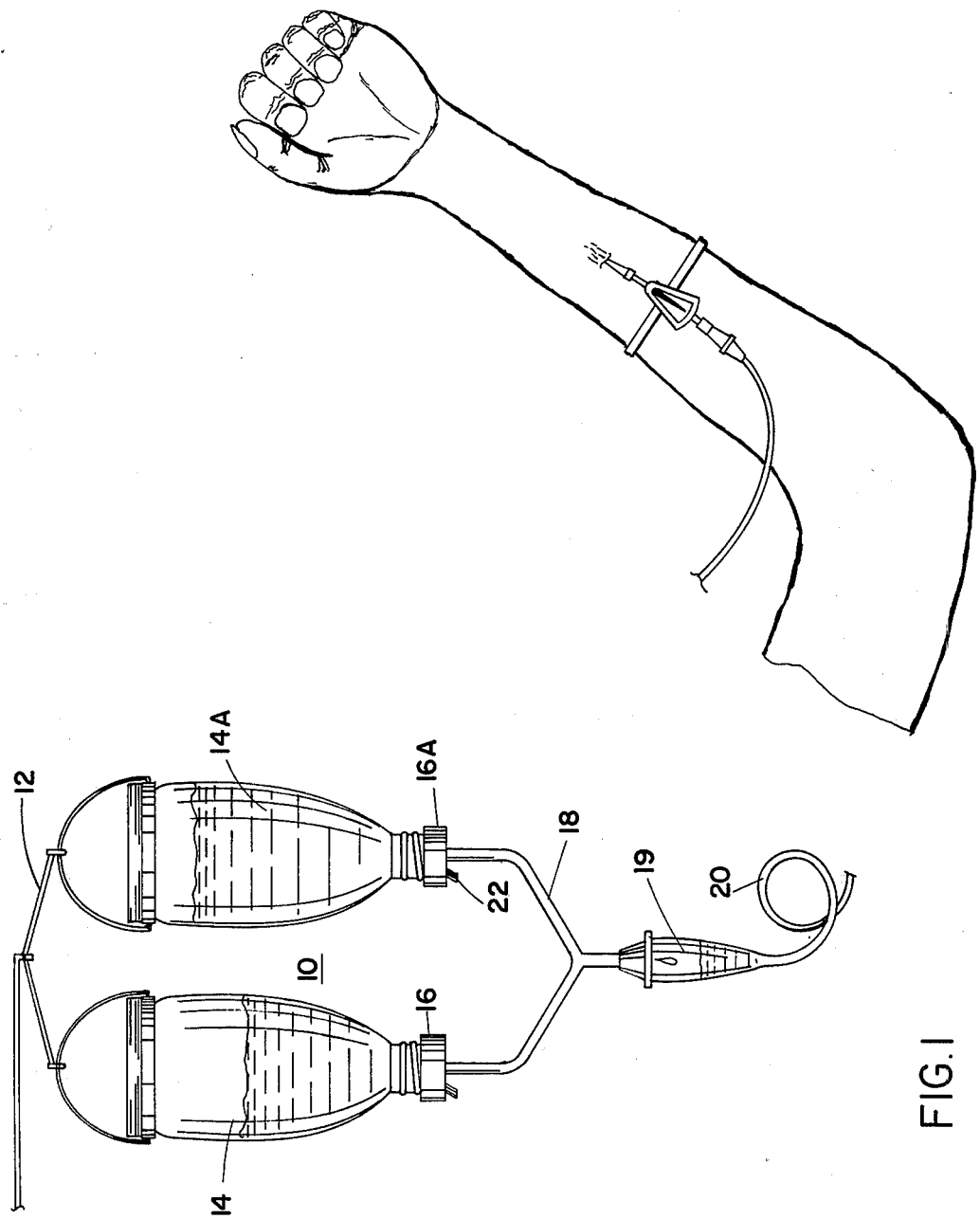
FIG. 1 is an overall illustration of the present invention adapted to and in use with commercial apparatus for the infusion of liquids into the body.

With particular reference to FIG. 1, a pair of conventional intravenous bottles or liquid containers 10 are supported in the conventional manner by an upstanding support pedestal 12. The bottles 10 are filled with a sterile liquid solution 14 and 14a intended is to be infused into a patient. For instance, the solution 14 may comprise a sugar, salt or mineral solution, and the solution 14a may be electrolytes or antibiotics to be added to the primary solution. Although an intravenous bottle is illustrated, the present invention may be used in any one of a number of infusion systems wherein a liquid is to be infused into the body of a patient. Thus, the solution 14 may be infused into any of the veins or into the arteries of the patient. The bottle 10 and solution 14 may be used as a renal infusion system wherein the patient is to be irrigated with water and/or antibiotics. Alternatively, blood may be metered from the bottle 10 into a patient or again the liquid may be an anesthetic.

The stopper 16 and 16a are connected to the bottles 10 and includes a spike for piercing the seal on the ends of the bottles. The spike includes an outlet aperture to allow the liquid solution 14 to flow from bottle 10 to the tubing 18. The liquid solutions 14 and 14a fall into a drip chamber 19 and flows down the flexible tube 20 for infusion into the patient. Generally, the end of tube 20 is connected to a needle inserted into the patient. Bottles 10 are generally comprised of glass or may be of the collapsible type. Tube 20 is generally comprised of plastic.

Stopper 16 includes an air inlet 22 also extending into the inverted bottle for venting of air or other gas into the bottle 10. The venting of air is to enable the replacement of the liquid solution 14 flowing from the bottle 10 with air for proper operation of the infusion system. An unimpeded air inlet is desired to enable the venting of air into the bottle. As noted above, however, air venting is not needed in a plastic collapsible bag used in lieu of the bottle 10. Since the bottle 10, caps 16, the Y tubing, drip chamber 19 and flexible tube 20 are all conventional and are widely used throughout hospitals, further detail description is not necessary. Also normally included with the commercial IV sets is a flow control mechanism either of the screw-in or the sliding ramp type. Since the present invention eliminates such a mechanism it is not shown.

In accordance with the general concepts of the invention a control/flowmeter valve is strapped to the arm of the patient. The end of the tubing 20 is fitted into the input side and a needle, catheter, needle set, or parenteral set is fitted into the output side. In this way the entire system is unimpeded — in no way is the fluid flowing through the line affected and only that fluid going into the body of the patient is measured. The overall system remains air tight and sterile.

Referring again to FIG. 1 and specifically to FIG. 2 there is illustrated the preferred embodiment of the present invention in operation with a conventional intravenous liquid infusion systems. Particularly the end 20a of the tubing 20 is normally fitted with a somewhat enlarged tubing adapted to have fitted thereon an injection needle or adapted to be inserted into a catheter in the body of a patient. The apparatus of the present invention is intermediate the output end 20a and the input end of injection needle 30.

The input end 26 of control/indicator valve 36 is of a size to be fitted directly into the output end of the enlarged tubing 20a. The other end 28 of the control/indicator valve is of a size to be fitted directly into the needle, catheter, needle set, or parenteral set 30. Interconnecting the input end 26 and the output end 28 of control/indicator valve 36 is a fluid passage (not seen). The fluid passage is controlled in opening (from full open to closed) in a conventional manner responsive to an interfitting rotating member. The control knob 32 is an open-shut control with a pointer 32a to indicate on the scale 24 the rate of fluid flow. In this embodiment the full span of the control valve is in the order of 60°. Hence, the points will vary from zero (off) to full scale (open) in an arc scale of approximately 60°.

The strap 40 is a wrist-band strap to hold in position the control/indicator and the injection needle. As shown in FIG. 2a, the strap is adjustable by the plurality of apertures 34a n in the straps one end and the plurality of capped inserts 34b n in the straps other end. The relative sizes of the apertures and inserts are such to permit ease of entry but nonetheless security when strapped. The length of the band, of course, varies with the size of the patients arm, and the length of the band also varies with its usage, that is, whether the injection is in the arm or the leg of the patient.

The female fitting 26 in the input side of control indicator is somewhat extended to permit capping with cap 26a as shown in FIG. 2b. In this way the entire assembly may remain in position at all times — not requiring new openings into the body and with the least inconvenience and discomfort to the patient.

It can be seen from the above the entire assembly is simple and relatively inexpensive. The liquid control flow indicator is a positive action valve with a quick turn-off. There is no changes in fluid flow due to changes in temperature, tube crimps, viscosity, or with time. Sterilization is maintained together with the assurance that there will be no air entering the line.

It is to be understood that while the detailed drawings and specific examples given describe preferred embodiments of my invention, they are for purposes of illustration only, that the apparatus of the invention is not limited to the precise details and conditions disclosed and that various changes may be made therein without departing from the spirit of the invention which is defined by the following claims:

What is claimed is:

1. Apparatus for administering medicated liquid to a patient including a container for the liquid, a drip chamber immediately adjacent to said container and connected thereto with a hose line, and an extended hose line connecting said fluid in the container through said drip chamber to a body insertable cannula, means for suspending said liquid container above the body of the patient for gravitational flow of said liquid through said drip chamber and said extended hose line; the improvement comprising:

liquid flow control means having an input fluid passage directly connected to the terminal end of said extended hose line opposite to that of said drip chamber, and an output fluid passage;

said control means including metering means for metering and indicating the liquid passing therethrough;

means for securing said control and metering means to the body of a patient adjacent to the point of entry of said body insertable cannula;

said output fluid passage in said control means directly connected to said body insertable cannula and;

valve means connected with said control means to vary the size of said fluid passage;

whereby said control and metering means controls and meters the fluid passage at the point of entry of said body insertable cannula.

2. Apparatus as set forth in claim 1 wherein said valve means further includes a scale for determining and indicating the size of said passage.

3. Apparatus as set forth in claim 2 wherein said valve means further comprises a manual adjustment for varying said passage from full to closed.

4. Apparatus as set forth in claim 3 wherein said manual adjustment is a rotatable knob.

5. Apparatus as set forth in claim 4 wherein said rotatable knob has a full span rotation of the order of 60°.

6. Apparatus as set forth in claim 5 wherein said rotatable knob includes a pointer and wherein said scale is in the order of a 60° arc.

7. Apparatus as set forth in claim 1 wherein said securing means is an adjustable strap.

* * * * *